United States Patent
Yoganathan et al.

(10) Patent No.: US 10,039,531 B2
(45) Date of Patent: Aug. 7, 2018

(54) SYSTEMS AND METHODS TO CONTROL THE DIMENSION OF A HEART VALVE

(75) Inventors: Ajit P. Yoganathan, Tucker, GA (US); Jorge Hernan Jimenez, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1507 days.

(21) Appl. No.: 12/097,318

(22) PCT Filed: Dec. 15, 2006

(86) PCT No.: PCT/US2006/062192
§ 371 (c)(1),
(2), (4) Date: Oct. 27, 2008

(87) PCT Pub. No.: WO2007/100409
PCT Pub. Date: Sep. 7, 2007

(65) Prior Publication Data
US 2009/0292353 A1 Nov. 26, 2009

Related U.S. Application Data

(60) Provisional application No. 60/750,559, filed on Dec. 15, 2005.

(51) Int. Cl.
*A61F 2/24* (2006.01)
*A61B 17/00* (2006.01)
(Continued)

(52) U.S. Cl.
CPC .... *A61B 17/00234* (2013.01); *A61B 17/0401* (2013.01); *A61F 2/2454* (2013.01);
(Continued)

(58) Field of Classification Search
CPC ............... A61F 2/2442; A61B 17/1285; A61B 17/00234; A61B 17/0401;
(Continued)

(56) References Cited

U.S. PATENT DOCUMENTS 3,656,185 A 4/1972 Carpentier
3,671,979 A 6/1972 Moulopoulos
(Continued)

FOREIGN PATENT DOCUMENTS

EP 0338994 10/1989
EP 0595791 5/1994
(Continued)

OTHER PUBLICATIONS

International Search Report and Written Opinion dated Oct. 12, 2007 for related PCT Application No. PCT/US2006/062185.
(Continued)

*Primary Examiner* — Gregory Anderson
(74) *Attorney, Agent, or Firm* — Troutman Sanders LLP; Ryan A. Schneider; Andrew C. Doherty

(57) ABSTRACT

The cinching apparatus (800) comprising: an anchoring component having a distal end a proximal end; the distal end of the anchoring component having an engaging member (805). A locking component (815) and a tension member (820) wherein the anchoring component is enabled to be positioned on a first target site of a tissue component and the locking component (815) is enabled to be positioned on a second target site of a tissue component of the heart, and the tension member (820) can be coupled to both the anchoring component and the locking component (815) to adjust the distance between the first and second target sites.

20 Claims, 12 Drawing Sheets

(51) Int. Cl.
*A61B 17/04* (2006.01)
*A61B 17/06* (2006.01)

(52) U.S. Cl.
CPC .......... *A61B 2017/00243* (2013.01); *A61B 2017/0404* (2013.01); *A61B 2017/0414* (2013.01); *A61B 2017/0417* (2013.01); *A61B 2017/0496* (2013.01); *A61B 2017/06052* (2013.01); *A61F 2/2445* (2013.01)

(58) Field of Classification Search
CPC ...... A61B 2017/0459; A61B 2017/048; A61B 2017/0496
USPC .............. 606/151, 153, 228–232; 623/2.11
See application file for complete search history.

(56) References Cited

U.S. PATENT DOCUMENTS

| | | |
|---|---|---|
| 4,055,861 A | 11/1977 | Carpentier et al. |
| 4,056,854 A | 11/1977 | Boretos et al. |
| 4,164,046 A | 8/1979 | Cooley |
| 4,217,665 A | 8/1980 | Bex et al. |
| 4,275,469 A | 6/1981 | Gabbay |
| 4,602,911 A | 7/1986 | Ahmadi et al. |
| 4,790,844 A | 12/1988 | Ovil |
| 4,917,097 A | 4/1990 | Proudian et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,165,120 A | 12/2000 | Schweich, Jr. et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,626,899 B2 | 9/2003 | Houser et al. |
| 6,629,534 B1 | 10/2003 | St. Goer et al. |
| 6,669,687 B1 | 12/2003 | Saadat |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,764,510 B2 | 7/2004 | Vidlund et al. |
| 6,790,230 B2 | 9/2004 | Beyersdorf et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,896,690 B1 | 5/2005 | Lambrecht et al. |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,986,775 B2 | 1/2006 | Morales et al. |
| 6,991,649 B2 | 1/2006 | Sievers |
| 7,018,406 B2 | 3/2006 | Seguin et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,144,363 B2 * | 12/2006 | Pai .............. A61B 17/00234 600/16 |
| 7,166,126 B2 | 1/2007 | Spence et al. |
| 7,166,127 B2 | 1/2007 | Spence et al. |
| 7,186,262 B2 | 3/2007 | Saadat |
| 7,247,134 B2 | 7/2007 | Vidlund et al. |
| 7,294,148 B2 | 11/2007 | McCarthy |
| 7,329,280 B2 | 2/2008 | Bolling et al. |
| 7,527,647 B2 | 5/2009 | Spence |
| 8,308,765 B2 * | 11/2012 | Saadat .............. A61B 17/0401 24/115 R |
| 2001/0034551 A1 | 10/2001 | Cox |
| 2002/0029080 A1 | 3/2002 | Mortier et al. |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 * | 5/2004 | Spence et al. ............ 623/2.36 |

(56) References Cited

U.S. PATENT DOCUMENTS

| | | |
|---|---|---|
| 2004/0122513 A1 | 6/2004 | Navia et al. |
| 2004/0133192 A1 | 7/2004 | Houser et al. |
| 2004/0152947 A1* | 8/2004 | Schroeder et al. ............ 600/37 |
| 2004/0153103 A1* | 8/2004 | Schwartz ........... A61B 17/0401 606/148 |
| 2004/0186566 A1 | 9/2004 | Hindrichs et al. |
| 2004/0193259 A1* | 9/2004 | Gabbay ....................... 623/2.11 |
| 2004/0249452 A1 | 12/2004 | Adams et al. |
| 2004/0249453 A1 | 12/2004 | Cartledge et al. |
| 2004/0260317 A1* | 12/2004 | Bloom et al. ................. 606/151 |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075719 A1 | 4/2005 | Berghiem |
| 2005/0075727 A1 | 4/2005 | Wheatley |
| 2005/0080402 A1 | 4/2005 | Santamore et al. |
| 2005/0131533 A1 | 6/2005 | Alfieri et al. |
| 2005/0137689 A1 | 6/2005 | Salahieh et al. |
| 2005/0143811 A1 | 6/2005 | Realyvasquez |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0261759 A1 | 11/2005 | Lambrecht et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020333 A1 | 1/2006 | Lashinski et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0052868 A1 | 3/2006 | Mortier et al. |
| 2006/0149368 A1 | 7/2006 | Spence |
| 2006/0167474 A1 | 7/2006 | Bloom et al. |
| 2006/0195012 A1 | 8/2006 | Mortier et al. |
| 2006/0195183 A1 | 8/2006 | Navia et al. |
| 2006/0229708 A1 | 10/2006 | Powell et al. |
| 2006/0241340 A1 | 10/2006 | Schroeder et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0118154 A1 | 5/2007 | Crabtree |
| 2007/0118213 A1* | 5/2007 | Loulmet ............ A61B 17/0401 623/2.1 |
| 2007/0123979 A1 | 5/2007 | Perier et al. |
| 2007/0129758 A1 | 6/2007 | Saadat |
| 2007/0162111 A1 | 7/2007 | Fukamachi et al. |
| 2007/0173930 A1 | 7/2007 | Sogard et al. |
| 2007/0203391 A1* | 8/2007 | Bloom ............ A61B 17/00234 600/37 |
| 2007/0208357 A1 | 9/2007 | Houser et al. |
| 2007/0213582 A1 | 9/2007 | Zollinger et al. |
| 2007/0255396 A1 | 11/2007 | Douk et al. |
| 2008/0027268 A1 | 1/2008 | Buckner et al. |
| 2008/0039935 A1 | 2/2008 | Buch et al. |
| 2008/0051807 A1 | 2/2008 | St. Goar et al. |
| 2008/0081942 A1 | 4/2008 | Pai et al. |
| 2009/0157174 A1 | 6/2009 | Yoganathan et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| EP | 0860151 | 8/1998 |
| EP | 1034753 | 9/2000 |
| FR | 2708458 | 8/1993 |
| WO | 199119456 | 12/1991 |
| WO | 199503757 | 2/1995 |
| WO | 199640006 | 12/1996 |
| WO | 199741801 | 11/1997 |
| WO | 199742871 | 11/1997 |
| WO | 199806329 | 2/1998 |
| WO | 199911201 | 3/1999 |
| WO | WO 1999/30647 | 6/1999 |
| WO | 199951169 | 10/1999 |
| WO | 199965423 | 12/1999 |
| WO | 200032105 | 6/2000 |
| WO | WO 2000/047139 | 8/2000 |
| WO | 200119292 | 3/2001 |
| WO | 200126586 | 4/2001 |
| WO | 200147438 | 7/2001 |
| WO | 200187191 | 11/2001 |
| WO | 200203892 | 1/2002 |
| WO | 2003020178 | 3/2003 |
| WO | 2003041617 | 5/2003 |
| WO | 2004004607 | 1/2004 |
| WO | WO 2004/112658 | 12/2004 |
| WO | 2005004753 | 1/2005 |
| WO | 2005034813 | 4/2005 |
| WO | 2005082278 | 9/2005 |
| WO | 2005110290 | 11/2005 |
| WO | 2006041877 | 4/2006 |
| WO | 2006133186 | 12/2006 |
| WO | 2007050506 | 5/2007 |
| WO | 2007100408 | 9/2007 |
| WO | WO2007/100408 | 9/2007 |
| WO | WO2007/100409 | 9/2007 |
| WO | WO2007/100410 | 9/2007 |
| WO | 2007131513 | 11/2007 |
| WO | 2008058940 | 5/2008 |
| WO | 2008063537 | 5/2008 |
| WO | 2008094469 | 8/2008 |
| WO | 2008098226 | 8/2008 |

OTHER PUBLICATIONS

International Search Report and Written Opinion dated Sep. 27, 2007 for related PCT Application No. PCT/US2006/062192.

International Search Report and Written Opinion dated Oct. 31, 2007 for related PCT Application No. PCT/US2006/062199.

Examination Report for related European Patent Application No. 06850306.9 dated Apr. 8, 2011.

Adams, David, et al., "Large Annuloplasty Rings Facilitate Mitral Valve Repair in Barlow's Disease", The Society of Thoracic Surgeons, vol. 82, pp. 2096-2101, 2006.

Alonso-Lei, F. et al., "Adjustable Annuloplasty for Tricuspid Insufficiency" The Annals of Thoracic Surgery, vol. 46, No. 3, pp. 368-369, Sep. 1988.

Bolling, Steven F. et al., "Mitral Valve Reconstruction in the Patient with Heart Failure", Heart Failure Reviews, vol. 6, pp. 177-185, 2001.

Bolling, Steven F. et al., "Surgical Alternatives for Heart Failure", The Journal of Heart and Lung Transplantation, vol. 20, No. 7, pp. 729-733, 2001.

Carpentier, Alain F. et al., "The "Physio-Ring": An Advanced Concept in Mitral Valve Annuloplasty", The Thirty-First Annual Meeting of The Society of Thoracic Surgeons, pp. 1177-1186, Jan. 30-Feb. 2, 1995.

"Carpentier-Edwards Classic Annuloplasty Ring With Duraflo Treatment Models 4425 and 4525 for Mitral and Tricuspid Valvuloplasty", Baxter Healthcare Corporation, pp. 1-6, 1998.

(56) References Cited

OTHER PUBLICATIONS

"Carpentier-Edwards Physio Annuloplasty Ring", Edwards Lifesciences LLC, pp. 1-2, 2003.
Cochran, Richard P. et al., "Effect of Papillary Muscle Position on Mitral Valve Function: Relationship to Homografts", The Society of Thoracic Surgeons, vol. 66, pp. S155-S161, 1998.
Flachskampf, Frank A. et al., "Analysis of Shape and Motion of the Mitral Annulus in Subjects With and Without Cardiomyopathy by Echocardiographic 3-Dimensional Reconstruction", The Journal of the American Society of Echocardiography, vol. 13, pp. 277-287, 2000.
Gatti, Giuseppe et al., "Preliminary Experience in Mitral Valve Repair Using the Cosgrove-Edwards Annuloplasty Ring", Interactive Cardiovascular and Thoracic Surgery, vol. 2, No. 3, pp. 256-261, 2003, http://icvts.ctsnetjournals.org/cgi/content/full/2/3/256.
Melo, J.Q. et al., "Atrioventricular Valve Repair Using Externally Adjustable Flexible Rings", The Journal of Thoracic and Cardiovascular Surgery, vol. 110, No. 5, pp. 1333-1337, Nov. 1995.
"MGH Study Shows Mitral Valve Prolapse Not a Stroke Risk Factor", Massachusetts General Hospital, pp. 1-3, Jun. 1999, http://www.mgh.harvard.edu/DEPTS/pubaffairs/releases/Jun_99_mitral_valve.htm.
Miller, Craig D., "Ischemic Mitral Regurgitation Redux—To Repair or to Replace?", The Journal of Thoracic and Cardiovascular Surgery, vol. 22, No. 6, pp. 1059-1062, Dec. 2001.
Salgo, Ivan S. et al., "Effect of Annular Shape on Leaflet Curvature in Reducing Mitral Leaflet Stress", Journal of the American Heart Association, Circulation 2002, vol. 106, pp. 711-717, Jul. 22, 2002, http://circ.ahajournals.org/cgi/reprint/106/6/711.
Seguin, J.R. et al., "Advance in Mitral Valve Repair Using a Device Flexible in Three Dimensions", The St. Jude Medical-Seguin Annuloplasty Ring, The American Society for Artificial Internal Organs Journal, vol. 42, No. 6, pp. M368-M371, 1996.
Smolens, Iva A. et al., "Mitral Valve Repair in Heart Failure", The European Journal of Heart Failure, vol. 2, pp. 365-371, 2000.
"Techniques for 3D Quantitative Echocardiography", University of Washington Cardiovascular Research & Training Center Cardiac Imaging Research Lab, pp. 1-4, http://depts.washington.edu/cvrtc/apples.html.
Watanabe, Nozomi, et al., "Mitral Annulus Flattens in Ischemic Mitral Regurgitation: Geometric Differences Between Inferior and Anterior Myocardial Infarction: A Real-Time 3-Dimensional Echocardiographic Study" Journal of the American Heart Association, Circulation 2005, vol. 112, pp. 458-468, Aug. 30, 2005, http://circ.ahajournals.org/cgi/content/full/112/9_suppI/I-458.

* cited by examiner

SYSTEMS AND METHODS TO CONTROL THE DIMENSION OF A HEART VALVE

BENEFIT & PRIORITY CLAIMS

This application is a 35 U.S.C. § 371 U.S. National Stage of International Application No. PCT/US2006/062192 filed 15 Dec. 2006, which claims priority to and the benefit of U.S. Ser. No. 60/750,559, filed 15 Dec. 2005. All of said prior applications are hereby incorporated by reference in their entireties as if fully set forth below.

CROSS REFERENCE TO RELATED APPLICATION

This application claims the benefit of U.S. Provisional Application No. 60/750,559, filed 15 Dec. 2005, which is hereby incorporated by reference in its entirety as if fully set forth below.

FIELD OF THE INVENTION

This invention relates generally to the field cardiac valve repair, and specifically to systems and methods to control the dimension of a heart valve.

BACKGROUND OF THE INVENTION

Cardiovascular disease accounts for nearly fifty percent of deaths in both the developed world and in developing countries. Indeed, the risk of dying from heart disease is greater than the risk from AIDS and all forms of cancer combined. Worldwide, cardiovascular disease causes 12 million deaths each year. It is the leading cause of death in the U.S., killing some 950,000 people each year. It also accounts for a significant amount of disability and diminished quality of life. Some 60 million people in the U.S. alone have some form of heart disease. Therefore, a great need exists for the advancement of devices and procedures to cure, treat, and correct a wide variety of forms of heart disease.

Normal heart function primarily relies upon the proper function of each of the four valves of the heart, which pass blood through the four chambers of the heart. The four chambers of the heart include the right atrium and left atrium, the upper chambers, and the right ventricle and left ventricle, the lower chambers. The four valves, controlling blood flow in the chambers, include the tricuspid, mitral, pulmonary, and aortic valves. Heart valves are complex structures that rely on the interaction of many components to open and close the valve. More particularly, each of the four valves of the heart have cusps or leaflets, comprised of fibrous tissue, which attach to the walls of the heart and aid in controlling the flow of blood through the valves. The mitral valve has two leaflets and the tricuspid valve has three leaflets. The aortic and pulmonary valves have three leaflets that are more aptly termed "cusps," stemming from their half moon shape.

The cardiac cycle involves the pumping and distribution of both oxygenated and deoxygenated blood within the four chambers. In systole, or the rhythmic contraction of the heart cycle, oxygenated blood, enriched by the lungs, enters the heart into the left atrium or left upper chamber. During diastole, or the resting phase of heart cycle, the left atrial pressure exceeds the left ventricle pressure; thus, oxygenated blood flows through the mitral valve, a one way inflow valve, into the left ventricle. The contraction of the left ventricle pumps the oxygenated blood through the aortic valve, into the aorta, and is passed on to the body. When the left ventricle contracts in systole, the mitral valve closes and the oxygenated blood passes into the aorta. Deoxygenated blood returns from the body via the right atrium. This deoxygenated blood flows through the tricuspid valve into the right ventricle. When the right ventricle contracts, the tricuspid valve closes and the deoxygenated blood is pumped through the pulmonary valve. Deoxygenated blood is directed to the pulmonary vascular bed for oxygenation, and the cardiac cycle repeats itself.

The performance of the cardiac cycle by the various components of the heart is a complex and intricate process. Deficiency in one of the components of the heart or deficiency in the performance of the cardiac cycle most often leads to one or more of the numerous different types of heart disease. One of the most prevalent heart disease conditions is mitral valve regurgitation. Mitral valve regurgitation has many levels of severity. After 55 years of age, some degree of mitral regurgitation is found in almost 20% of men and women who have an echocardiogram. Mitral valve regurgitation, or mitral regurgitation, is a condition in which the mitral valve does not close tightly, thereby allowing blood to flow backward in your heart.

FIG. 1 provides an illustration of a normal mitral valve 101. As shown in FIG. 1, the mitral valve 101 includes a mitral annulus 105, an anterior mitral leaflet 110 and a posterior mitral leaflet 115, the chordae tendineae 120, and the medial and lateral papillary muscles, 135 and 140. The term mitral annulus refers to the elliptical region of the valve leaflet attachment contiguous with the base of the left atrium. The mitral annulus 105 is composed of an anterior mitral annulus 125 and a posterior mitral annulus 120. The mitral annulus 105 is saddle shaped with the basal portions of the saddle located medially and laterally. Attached to the anterior mitral annulus 125 is the anterior mitral leaflet 110 and attached to the posterior mitral annulus 130 is the posterior mitral leaflet 115. The regions where the anterior mitral leaflet 110 and the posterior mitral leaflet 115 meet are termed the lateral commissure 145 and the medial commissure 150.

In a normal mitral valve, when the atrial pressure exceeds the ventricular pressure, the valve leaflets open into the ventricle. When the ventricle pressure increases, the leaflets meet and close, covering the area of the valve annulus. Therefore, in the diagram shown in FIG. 1, anterior mitral leaflet 110 and the posterior mitral leaflet 115 will open during diastole to allow blood to flow through the mitral valve 101. Conversely, the anterior mitral leaflet 110 and the posterior mitral leaflet 115 will overlap and close the mitral valve 101 to prevent regurgitation, or backflow of blood, into the left atrium during systole.

The function of an atrioventricular valve, like the mitral valve, involves the complex interaction of numerous components, including the leaflets, chordae tendineae, and the papillary muscles. If one of the components or functions of the complicated interaction fails, then mitral valve regurgitation can result. For example, excess leaflet tissue, inadequate leaflet tissue, or restricted motion of the leaflets can lead to mitral regurgitation. Prolonged and/or severe mitral valve regurgitation can result in an overworked left ventricle. Overworking the left ventricle can lead to left ventricle enlargement and dysfunction resulting in heart failure. Mitral valve regurgitation is a progressive condition that, if not corrected, can be fatal.

Surgical treatment of ischemic mitral regurgitation (IMR) continues to be hampered by suboptimal clinical results and excessive long-term mortality. Mitral valve repair is preferred to valve replacement for most causes of mitral regurgitation but remains challenging for patients with IMR. Currently, small ring annuloplasty represents the standard mitral repair technique for IMR. Newer reparative techniques have been proposed to address this challenging disease.

U.S. Pat. No. 7,087,064 to Hyde ("'064 patent") describes a conventional technique for the treatment of mitral valve regurgitation, involving the use of a percutaneously deployable ligament. FIG. 2 provides an illustration of the ligatures of the '064 patent deployed in a mitral valve. As described in the '064 patent, the ligatures are percutaneously deployed, through the blood vessels, veins, or arteries into the heart. After deployment, the ligatures are then attached to the fibrous ring of the mitral valve on opposite sides of the mitral valve. The placement of ligatures that are smaller in diameter than the mitral valve annulus serves to constrict, reshape or reduce the circumference of the mitral valve.

As an alternative to the passive ligature method of the '064 patent, an experimental technique of Septal-Lateral Annular Cinching (SLAC) with a central transannular suture has shown some positive results. SLAC presents many potential advantages in comparison to more conventional techniques of treating heart dysfunctions and avoiding congestive heart failure. Conventional approaches and devices of treatment of the mitral valve have often resulted in a modification of the normal function of the valve. For example, some techniques treat mitral valve regurgitation by freezing the posterior leaflet of the valve, thus converting the bi-leaflet valve into a uni-leaflet valve. In a non-limiting example, ring annuloplasty can prevent acute ischemic mitral regurgitation, but it also abolishes normal mitral annular and posterior leaflet dynamics. Ring annuloplasty, and other similar techniques, can lead to the deterioration of the performance of the mitral valve, including a loss of annular flexibility and the creation of a transvalvular gradient. This type of technique modifies or alters the normal function of the mitral valve. SLAC, on the other hand, can be implemented to preserve the physiologic dynamics of the mitral valve and its leaflets. Furthermore, SLAC can help to maintain the physiologic mitral annular morphology for proper function.

A recent study focused on the use of a conventional SLAC implementation to treat acute ischemic mitral regurgitation in animal hearts, illustrated the potential advantages offered by SLAC techniques. Timek T A et al., *J Thorac Cardiovasc Surg.*, 2002 May; 123(5):881-8. The results of the study illustrated an average of a 22% (+/−10%) reduction in mitral annular septal-lateral dimension. This study concluded that this reduction in dimension reduced the acute ischemic mitral regurgitation while allowing near-normal mitral annular and posterior leaflet dynamic motion. Furthermore the study postulated that SLAC may represent a simple method for the surgical treatment of ischemic mitral regurgitation, either as an adjunctive technique or alone, which helps preserve physiologic annular and leaflet function.

Another conventional SLAC technique is disclosed in U.S. Patent Publication No. 2005/0143811 to Realyvasquez ("'811 Publication"). The '811 Publication discloses the implementation of SLAC using percutaneous deployment. FIG. 3 provides an illustration of the conventional device used to implement the SLAC technique disclosed in the '811 Publication. The device 50 shown in FIG. 3, is described in the '811 Publication as being delivered using a percutaneous intravascular catheter through the inter-atrial septum. Once the device is delivered, the two wired stents 52 are deployed and allowed to expand. The anterior portion of the stent 52 is attached to the annulus temporarily with the tines anchored to the wire. The posterior portion is anchored to the posterior annulus with similar tines. Once the stent is in proper position, the wires are re-enforced to their position with transvascular delivered fasteners to the posterior and anterior annular attachment points.

The device 50 disclosed in the '811 Publication includes a ratchet mechanism 60. This ratchet mechanism can be activated by the catheter that delivered the device 50. The '811 Publication describes that the catheter attached to ratchet mechanism 60 is turned in a counter clockwise direction, activating the ratchet mechanism 60. The rotation of the ratchet mechanism 60 operates to move the two wired stents 52 toward the center of the device 50. The '811 Publication discloses that the reduction in the distance between two wired stents 42 attached to the anterior annulus and the posterior annulus will serve to achieve the effect of septal-lateral annular cinching.

While the devices of the prior art are suitable for their intended purposes, they suffer from many drawbacks and fail to meet the demands of interventional cardiologists, cardiovascular surgeons, and the patients on whom they operate. Significantly, a need still exists for a minimally invasive device and associated technique to correct a deficient heart valve. More particularly, a need exists for a minimally invasive device and associated technique to restrict the septal-lateral diameter of an atrioventricular valve. Furthermore, the minimally invasive device and associated technique must be capable of implementation on a beating heart. It is highly desired to have a device capable of restricting the septal-lateral diameter of an atrioventricular valve which can be implemented in a variety of methods, including thoracoscopically and percutaneously.

Therefore, it would be advantageous to provide an apparatus and method for improving valve competence.

Additionally, it would be advantageous to provide an apparatus and method for restricting the dimension of a heart valve.

Additionally, it would be advantageous to provide an apparatus and method for correcting mitral valve regurgitation by restricting the diameter of a heart valve in a beating heart.

Additionally, it would be advantageous to provide an apparatus and method for restricting the diameter of a valve of a beating heart capable of being implemented in a minimally invasive manner.

Additionally, it would be advantageous to provide an apparatus delivered with a long arm or steerable needle from outside the heart for restricting the diameter of a valve of a beating heart.

Additionally, it would be advantageous to provide an apparatus capable of incrementally decreasing the septal-lateral diameter of an atrioventricular valve of a beating heart.

Additionally, it would be advantageous to provide an apparatus capable of decreasing the diameter of a heart valve in increments over an extended period of time.

Additionally, it would be advantageous to provide a method of reducing the dimension of a heart valve that enables a surgeon to easily access components used in an earlier surgery to later further restrict the dimension of the heart valve.

Additionally, it would be advantageous to provide a method of reducing the dimension of a heart valve that allows repeat reductions over an extended period of time.

Additionally, it would be advantageous to provide an apparatus and method for improving the morphology of beating heart valve without altering the physiologic dynamics of the heart valve.

BRIEF SUMMARY OF THE INVENTION

The present invention describes methods and apparatus to control the dimension of a heart valve. An exemplary embodiment of the present invention provides a method of improving valve morphology. The method first involves attaching an anchoring component to a first target site on a tissue component of a heart. Then, a locking component is attached to a second target site on the tissue component of the heart. Subsequently, a tension member is coupled to the anchoring component and the tension member is coupled to the locking component. Then the distance between the first target site and the second target site is adjusted by activating the tension member. The tension member can then be locked into place with the locking component.

These and other objects, features and advantages of the present invention will become more apparent upon reading the following specification in conjunction with the accompanying drawing figures.

DETAILED DESCRIPTION OF PREFERRED EMBODIMENTS

Figure 1:
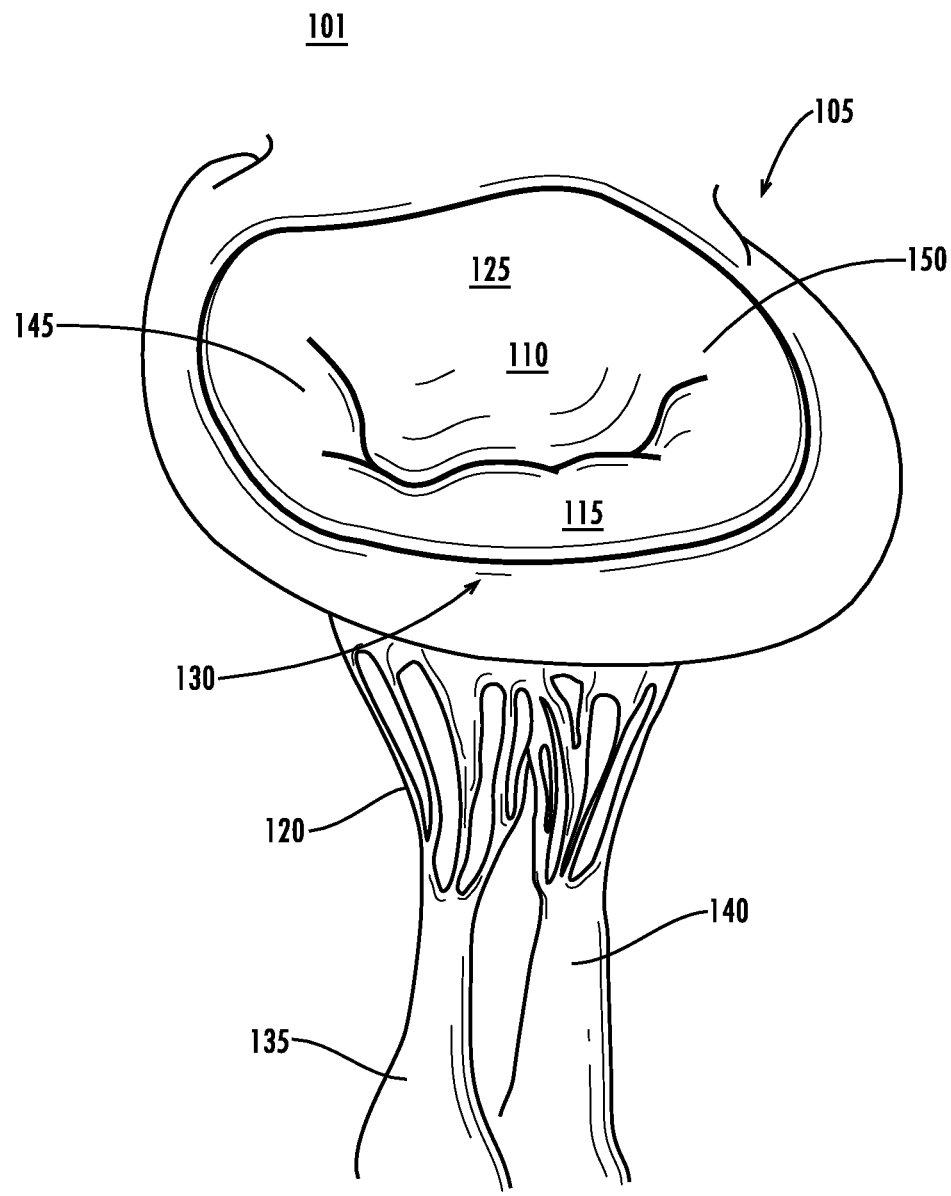
FIG. 1 provides an illustration of a normal mitral valve 101.
Figure 2:
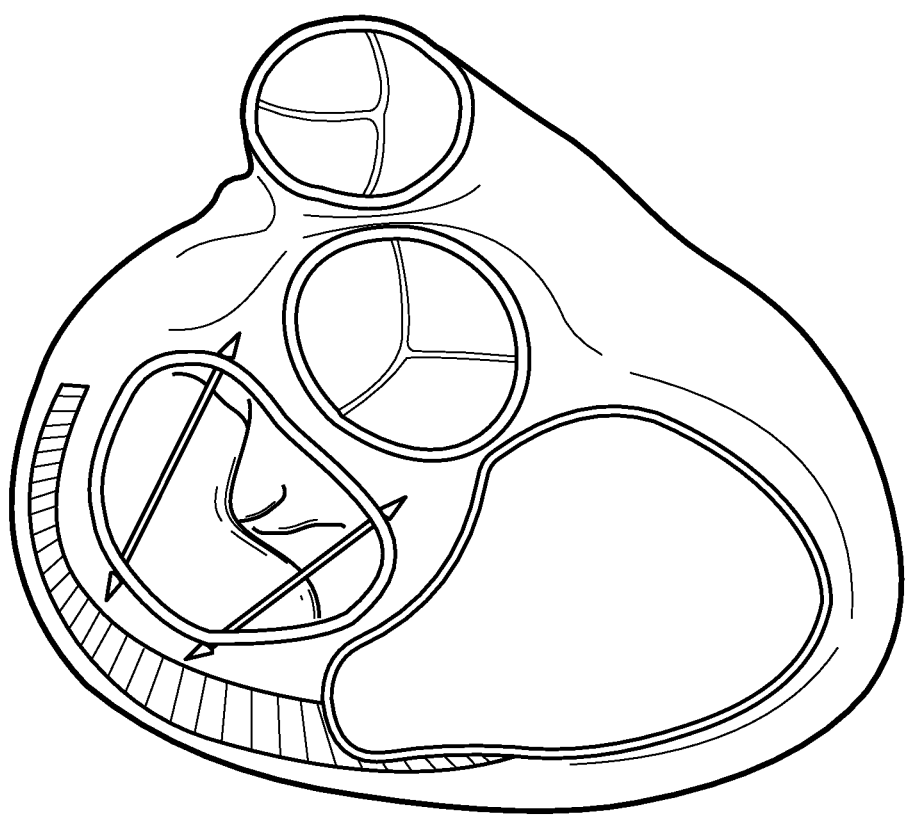
FIG. 2 provides an illustration of a conventional valve correction device disclosed in the prior art.
Figure 3:
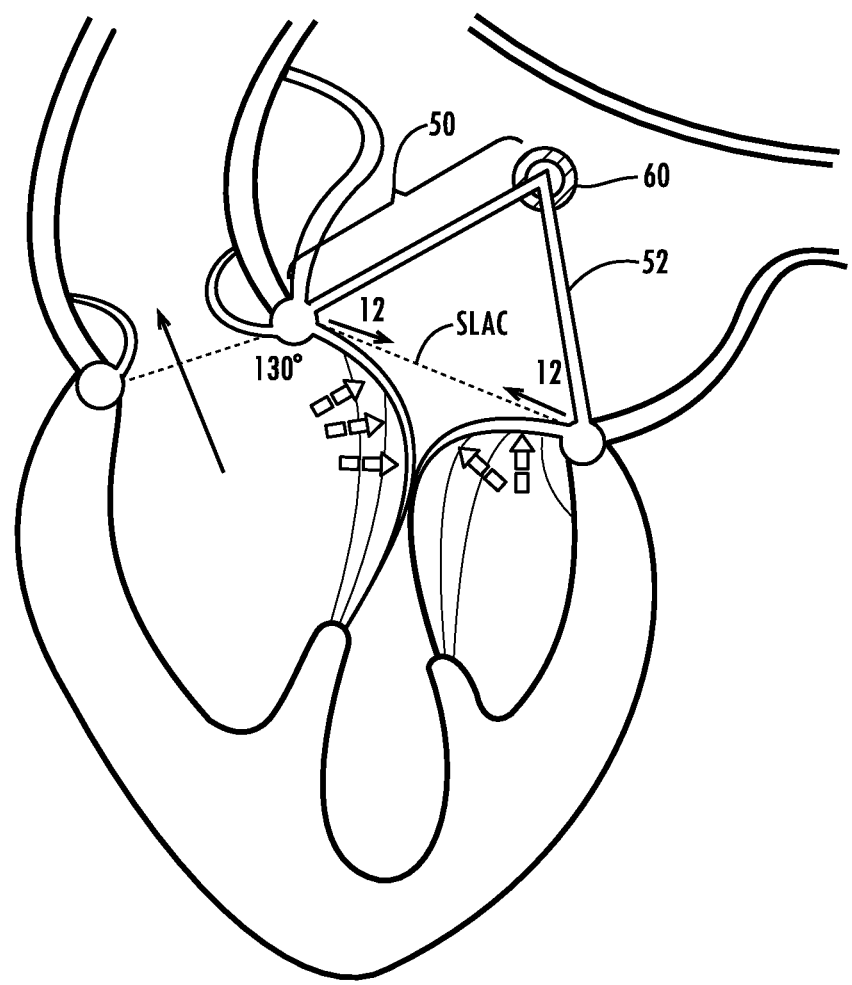
FIG. 3 provides an illustration of the conventional device used to implement the SLAC technique disclosed in the prior art.

The present invention addresses the deficiencies in the prior art by providing a minimally invasive apparatus and method for improving valve morphology. The medical device and method of improving valve morphology disclosed herein can enable an incremental reduction in the distance between two target sites within a valve in the heart. The reduction in the distance between two target sites within a valve in the heart can improve and/or restore the competence of the valve.

An exemplary embodiment of the present invention provides a method of improving valve morphology. The method first involves attaching an anchoring component to a first target site on a tissue component of a heart. Then, a locking component is attached to a second target site on the tissue component of the heart. Subsequently, a tension member is coupled to the anchoring component and the tension member is coupled to the locking component. Then the distance between the first target site and the second target site is adjusted by activating the tension member. The tension member can then be locked into place with the locking component.

An exemplary embodiment of the method of improving valve morphology can be used to treat, and in some instances correct, mitral valve regurgitation. For example, and not limitation, the shortening of the distance between the first target site and the second target site can reduce the septal-lateral diameter of a mitral valve. This reduction in the septal-lateral diameter of a mitral valve can help achieve mitral competence by enabling the overlap of mitral leaflets during systole. Furthermore, the reduction in the septal-lateral diameter can cease or aid in reducing the backflow of blood into the left atrium from the left ventricle during systole.

In addition, to improving the morphology of a mitral valve, the methods and devices enabled by the present invention can be used to improve the competence of other valves. An exemplary embodiment of the method of improving valve morphology can be used to treat, and in some instances correct, aortic valve regurgitation. Alternative embodiments of the method of improving valve morphology can be used to improve the competence of the pulmonic valve and the tricuspid valve.

The method of improving valve morphology in accordance with the present invention is a minimally invasive procedure that can be implemented on a beating heart. Furthermore, the method of improving valve morphology in accordance with the present invention can implemented by a variety of procedures or a combination of a variety of procedures, including thoracoscopic, endovascular, and percutaneous deployment. Those of skill in the art will appreciate that the embodiments of the methods of improving valve morphology and the associated apparatus described herein are exemplary embodiments and have merely been provided as representative examples.

In an exemplary embodiment of the present invention, a cinching apparatus is provided that has an anchoring component with a proximal end and a distal end. The proximal end of the anchoring component has an attaching member enabled to communicate with a tissue component of a heart. The locking component also has an attaching member enabled to communicate with the tissue component of a heart. The cinching apparatus also provides a tension member. The anchoring component is enabled to be positioned on a first target site of a tissue component of the heart, the locking component is enabled to be positioned on a second target site of the tissue component of the heart, and the tension member can be coupled to both the anchoring component and the locking component. The tension member can be activated to adjust the distance between the first target site and the second target site and fixed by the locking component.

In an exemplary embodiment, the tension member is activated by pulling the tension member to adjust the distance in a manner that reduces the distance between the first target site and the second target site. For example, and not limitation, a surgeon could pull the tension member so as to reduce the distance and the lock the tension member into place.

An exemplary embodiment of the cinching apparatus includes one or more anchoring components, locking components, and tension members. The components can be utilized in the method of improving valve morphology in accordance with the present invention. In the exemplary embodiment, the various elements of the cinching apparatus are composed of a biocompatible material. The biocompatible material can be, but is not limited to, biocompatible metals or biocompatible polymers. Those of skill in the art will appreciate that the cinching apparatus could be constructed of a wide variety of biocompatible materials, without detracting from the scope of the invention.

The anchoring component is a device capable of attachment to tissue. In an exemplary embodiment, the anchoring component has a proximal end and a distal end. The terms proximal and proximate are used herein to describe a position which is in the relative vicinity of another position, including a range of vicinity positions through and including being directly adjacent or abutting another position. The term distal is used herein to describe a position which is situated a relative distance away from another position. Thus, the terms proximal/proximate and distal are used herein as spatial relation references and are not used to describe positions upstream or downstream in the flow of blood.

The proximal end of the anchoring component, in exemplary embodiment, can be enabled to engage tissue. For example, and not limitation, the proximal end of the anchoring component is a surface or rod at an angle with the main body of the anchoring component. The angle of the surface or rod allows this surface to produce interference, or clamp onto, a tissue component. In alternative embodiment, the anchoring component can have a proximal end with an umbrella configuration capable of piercing a tissue surface. Another embodiment provides an anchoring component with legs capable of embedding into a tissue surface. Those of skill in the art will appreciate that the proximal end of the anchoring component could be a variety of different components capable of attaching to a tissue surface.

In an exemplary embodiment, the central section of the anchoring system is a rod, wire, or many suitable elongated bodies. On the distal side of the anchoring component there is an engaging member or surface. This member is designed to couple with the tension member or rod. The coupling member in its preferred embodiments is a loop, a screwing surface, a hook, a clamp, a docking orifice, or many other suitable components. The anchoring component can be delivered endovascularly using a catheter or through a porthole in a heart chamber using a long arm delivery device or a steerable needle. Those of skill in the art will appreciate that the devices and tools used to implement the methods of the present invention can vary with the type of implementation. For example, those of skill in the art will appreciate that a long arm device can many different types of devices which enable a minimally invasive delivery of a component.

Figure 4A:
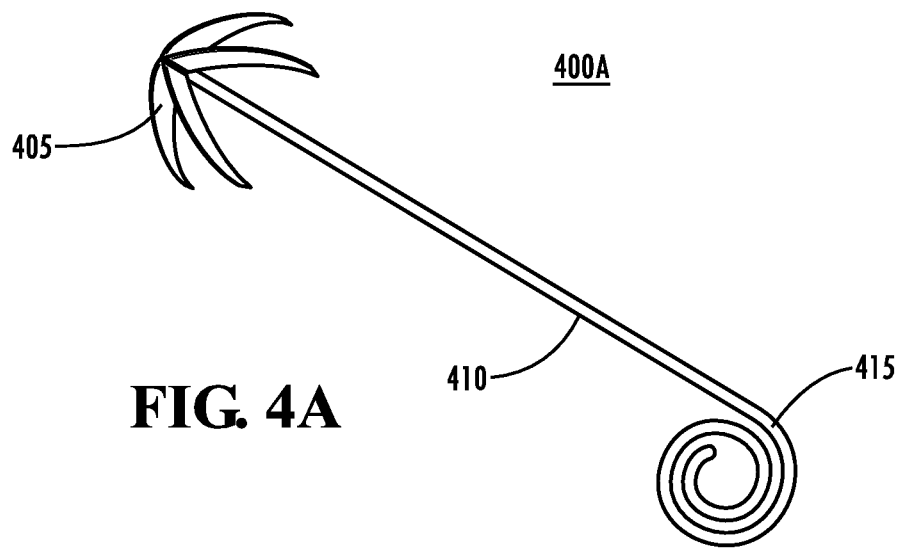
FIG. 4A provides an illustration of an exemplary embodiment of an anchoring component 400A in accordance with an exemplary embodiment of the present invention.

FIG. 4A provides an illustration of an exemplary embodiment of an anchoring component 400A in accordance with an exemplary embodiment of the present invention. The anchoring component 400A shown in FIG. 4A has an attaching member 405 at the proximal end of the device 400A. This attaching member 405 is capable of engaging and piercing a tissue component. In the exemplary embodiment depicted in FIG. 4A, the attaching member 405 is an umbrella structure. The central section of anchoring device 400A is a rod member 410.

The anchoring device 400A shown in FIG. 4A also has an engaging member 415 at the distal end of the device 400A. This engaging member 415 is capable of connecting, terminating, or fixating a tension member or other medium. As shown in the exemplary embodiment in FIG. 4A, the engaging member 415 can be a pigtail shaped member. This pigtail shaped member is advantageous because it can be deployed after the engaging member 415 has been inserted through a tissue component. In an exemplary embodiment, the engaging member 415 can be inserted through a tissue component in a substantially planar form and then deployed into a pigtail configuration. Those of skill in the art will appreciate that the engaging member 415 can be provided in many forms without detracting from the scope of the invention.

Figure 4B:
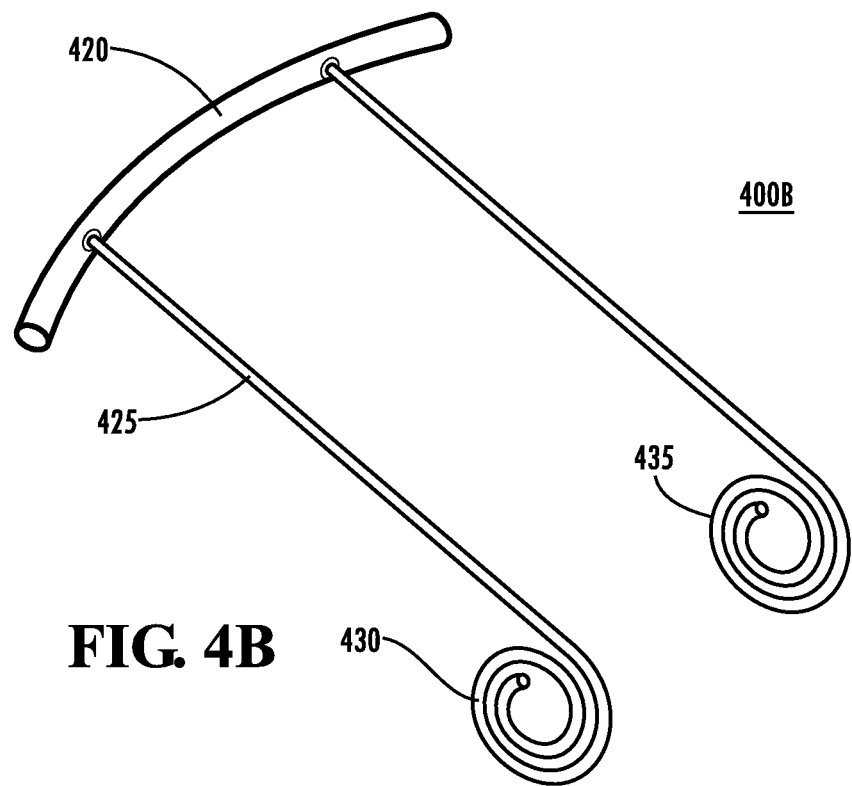
FIG. 4B provides an illustration of an alternative embodiment of an anchoring component 400B in accordance with the present invention.

FIG. 4B provides an illustration of an alternative embodiment of an anchoring component 400B in accordance with the present invention. The proximal end of the alternative embodiment of the anchoring component 400B shown in FIG. 4B has an attaching member 420 that is a rod shaped member. This rod shaped attaching member 420 can interface with a tissue surface. The exemplary embodiment of the anchoring component 400B has two engaging members, 430 and 435. These engaging members, 430 and 435, as shown in FIG. 4B can be pigtail shaped members capable of coupling to the tension member. In a non-limiting example, once positioned within the heart chamber, the engaging member 430 can be coupled to one tension member while the engaging member 435 can be coupled to a different tension member. Those of skill in the art will appreciate the two exemplary embodiments of anchoring components, 400A and 400B, shown in FIGS. 4A and 4B, are provided as representative examples, and the anchoring component could be implemented in a variety of alternative devices.

Figure 5:
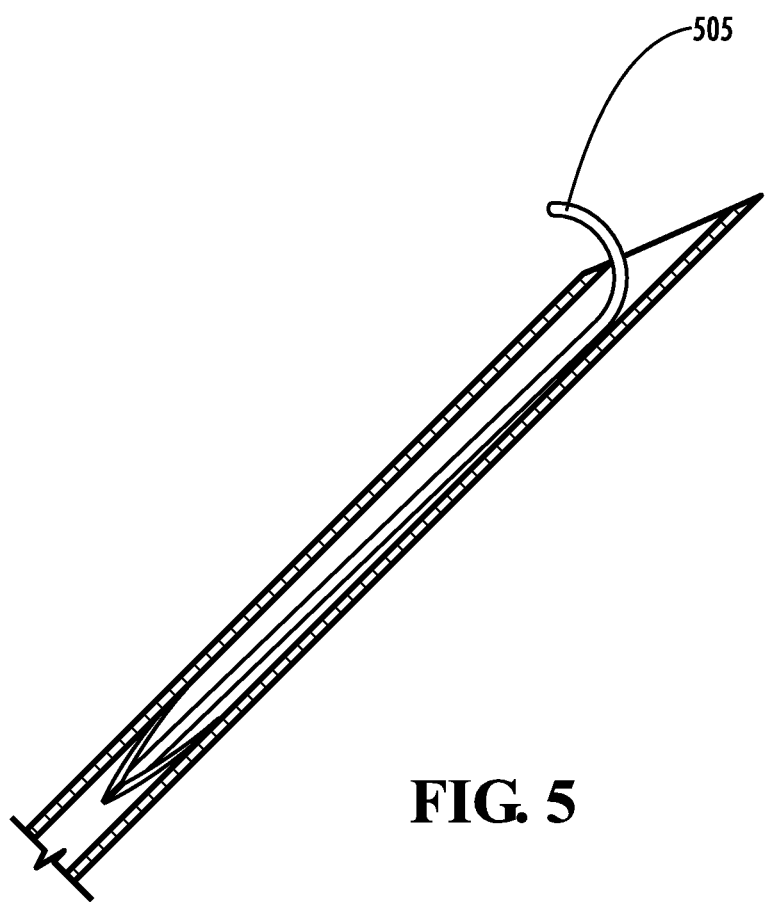
FIG. 5 provides an illustration of an exemplary embodiment of the engaging member 505 an anchoring component prior to deployment in accordance with an exemplary embodiment of the present invention.

FIG. 5 provides an illustration of an exemplary embodiment of the engaging member 505 an anchoring component prior to deployment in accordance with an exemplary embodiment of the present invention. The engaging member 505 shown in FIG. 5 is enabled to be delivered in an substantially planar form. The exemplary embodiment of the engaging member 505 can be delivered within a steerable needle or other suitable delivery device. In this manner, the engaging member 505 is enabled to pierce a tissue component in a substantially planar form. Once the engaging member 505 has pierced the tissue component, it can be deployed. For example, and not limitation, the engaging member 505 can pierce the posterior mitral annulus from the left ventricle into the left atrium. Once the engaging member 505 is within the left atrium, in an exemplary embodiment, it can be pushed through the lumen in excess to form a pigtail shaped member. This pigtail shaped member provides the necessary structure for the engaging member 505 to which a tension member can later be attached.

Figure 6A:
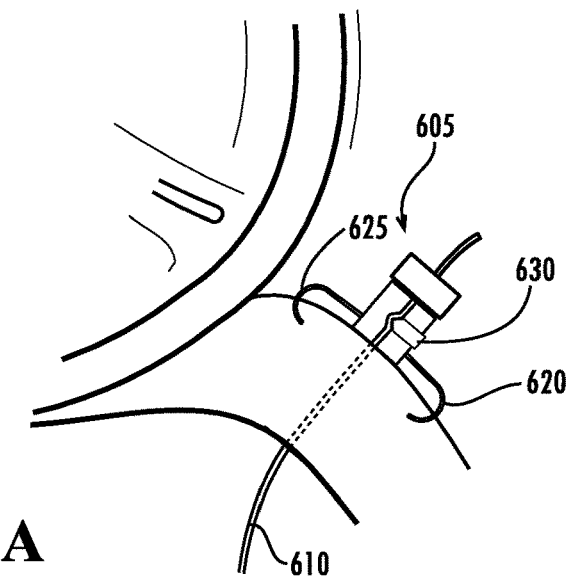
FIG. 6A provides an illustration of an exemplary embodiment of a locking component 605 in accordance with an exemplary embodiment of the present invention.

FIG. 6A provides an illustration of an exemplary embodiment of a locking component 605 in accordance with an exemplary embodiment of the present invention. In an exemplary embodiment, the locking component 605 can engage the outer surface of the heart or the cartilage on the trigone and other areas. The piercing components that enable the locking component 605 to engage can be a hook, umbrella, interference surface, a plurality of expandable legs, or many other suitable components. The locking component 605 can also have a lock system which can lock a tension member 610 and prevent movement when engaged and therefore restrict the diameter of the valve. In the exemplary embodiment shown in FIG. 6A, the locking component 605 has a lock system 630 that provides a pin compression system. As shown, the pin of the locking system 630 can be moveably positioned to lock or unlock the tension member 610.

In an exemplary embodiment, the locking component 605 can be attached at many suitable target sites on a tissue component of the heart. For example, and not limitation, in one embodiment the locking component 605 can be attached to a target site on a mitral annulus which is substantially opposite the location at which an anchoring component has been attached to the mitral annulus. The locking component 605 can have piercing components, such as 620 and 625, to pierce a tissue component and anchor the locking component 605 to the tissue component. In the exemplary embodiment shown in FIG. 6A, the piercing components 620 and 625 have pierced the left atrial wall near the anterior mitral annulus and adjacent to the wall of the aorta.

The locking component 605 can provide a conduit through which a tension member 610 can be passed. In an exemplary embodiment, a tension member 610 can be passed through the locking component 605 and enter the left atrium. In this exemplary embodiment, the tension member 610 can have an engaging distal end that can be coupled to the engaging member 415 of the anchoring component 400A (FIG. 4A). Once the tension member 610 is coupled to the anchoring component 400A, it can be advanced such that the distance between the anchoring component 400A (FIG. 4A) and the locking component 605 is reduced. After the distance has been reduced a desired amount, the locking system 630 of the locking component 605 can lock the tension member 610 into place. In an exemplary embodiment, the surgeon performing the method of improving valve morphology in accordance with the present invention can pull the tension member 610 from a position external to the patient's body and then lock the tension member 610 into place with the locking component 605.

In an exemplary embodiment, the locking component 605 is also enabled to be unlocked. Thus, if it is later desired to alter the distance between the locking component 605 and the anchoring component, the tension member 610 can be unlocked from the locking component 605. In a non-limiting example, the tension member 610 can be advanced to further reduce the distance between the locking component 605 and the anchoring component and then locked into place again.

Figure 6B:
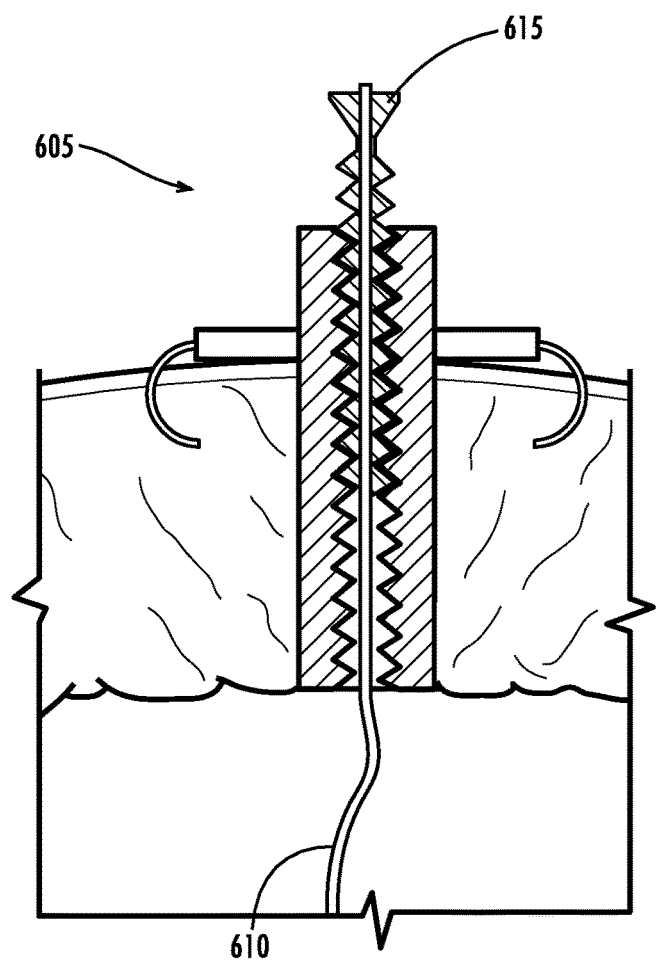
FIG. 6B provides an illustration of an alternative embodiment of a locking component 605 in accordance with an exemplary embodiment of the present invention.

FIG. 6B provides an illustration of an alternative embodiment of a locking component 605 in accordance with an exemplary embodiment of the present invention. As shown in FIG. 6B, the alternative embodiment of the locking component 605 can incorporate a screw component 615 to advance the tension member 610. Thereby, a surgeon can provided with the ability to advance the screw component 615 from a position external to the patient's body and advance the tension member 610 to reduce the distance between the locking component 605 and the anchoring component 400A (FIG. 4A). When then tension member 610 has been advanced the desired distance, the screw can be released. The stationary screw component 615 can then lock and maintain the tension member 610. Additionally, the screw component 615 can be re-accessed to further advance the tension member 610 and lock the tension member 610 into a new position.

Figure 7:
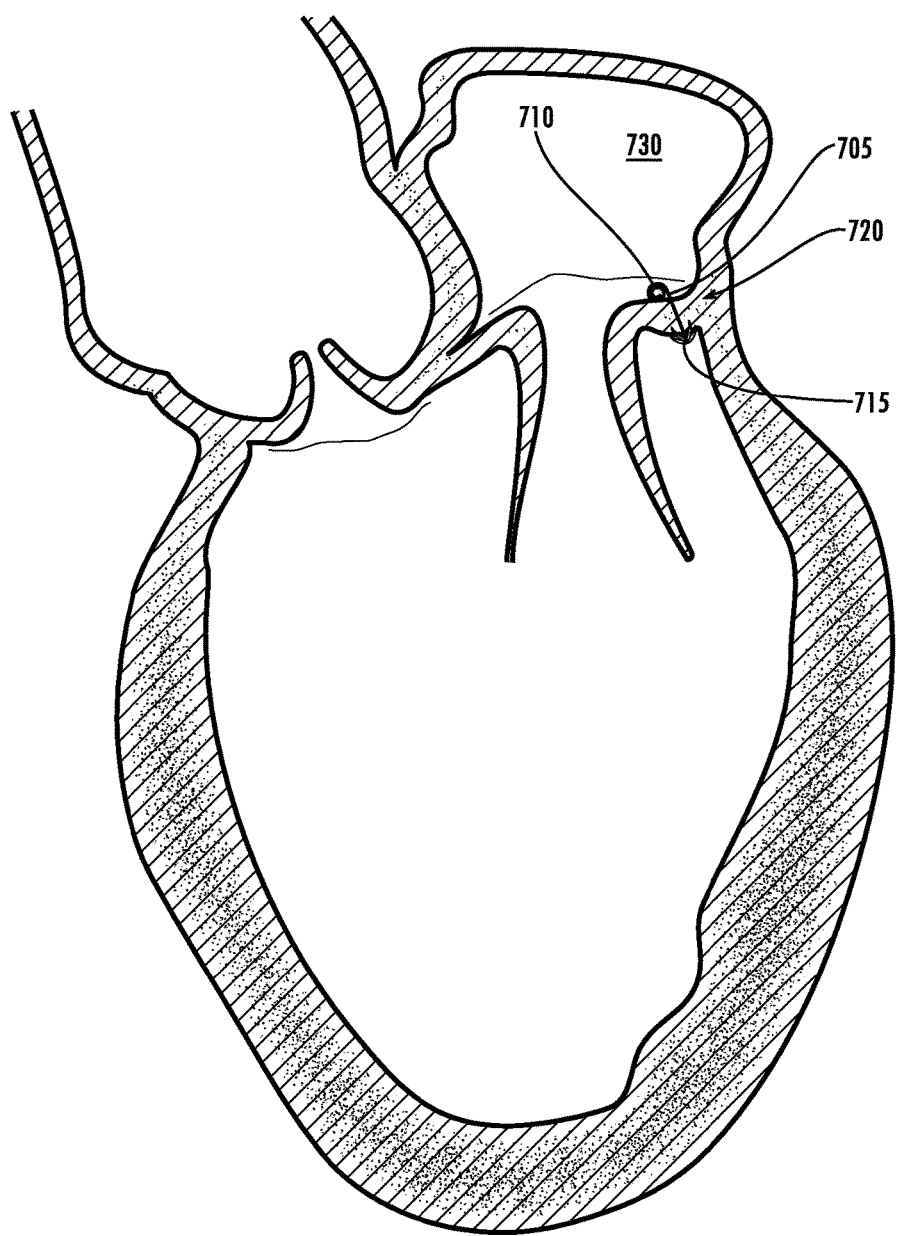
FIG. 7 provides an illustration of an exemplary embodiment of an anchoring component 705 in accordance with an exemplary embodiment of the present invention.

FIG. 7 provides an illustration of an exemplary embodiment of an anchoring component 705 in accordance with an exemplary embodiment of the present invention. In the exemplary implementation depicted in FIG. 7, the anchoring component 705 has been implanted through the posterior mitral annulus 720. For example, and not limitation, the anchoring component 705 can be delivered endovascularly using a catheter. Furthermore, the anchoring component 705 can be delivered in a condensed form and later deployed once in position. In a non-limiting example, the anchoring component 705 is delivered into the left ventricle. The anchoring component 705 can then be inserted from the left ventricle into the posterior mitral annulus 720 at a target site. Thus, the engaging component 710 of the anchoring component 705 can be caused to pierce the posterior mitral annulus 720 at a target site. Once the engaging component 710 pierces the posterior mitral annulus and enters the left atrium 730, the attaching member 715 of the anchoring component 705 can be attached to the posterior mitral annulus 720. In this manner the anchoring component 705 is lodged onto the posterior mitral annulus 720 with the engaging component 710 protruding into the left atrium 730.

In an alternative embodiment of the method of improving valve morphology, the anchoring component 705 can be delivered through the left atrium 730. In a non-limiting example, the anchoring component 705 can be attached to a catheter and percutaneously deployed into the left atrium 730. After the anchoring component 705 has been introduced into the left atrium 730, it can be caused to pierce the posterior mitral annulus 720 at a target site. In an exemplary embodiment, the attaching member 715 of the anchoring component 705 can be caused to pierce the mitral annulus 720 at a target site and protrude into the left ventricle. In this manner, the anchoring component 705 is lodged onto the posterior mitral annulus 720 at a target site.

Those of skill in the art will appreciate that the exemplary embodiment shown in FIG. 7 provides only one example of the implementation of an anchoring component in accordance with the present invention. For example, and not limitation, with respect to the posterior of the mitral valve, it is possible to place the anchoring component anywhere on the posterior mitral annulus or the myocardium proximate to the posterior mitral annulus. With respect to the anterior of the mitral valve, it is possible to place the anchoring component on anywhere on the anterior mitral annulus, the myocardium proximate the anterior mitral annulus or the fibrous trigone proximate the anterior mitral annulus.

Figure 8:
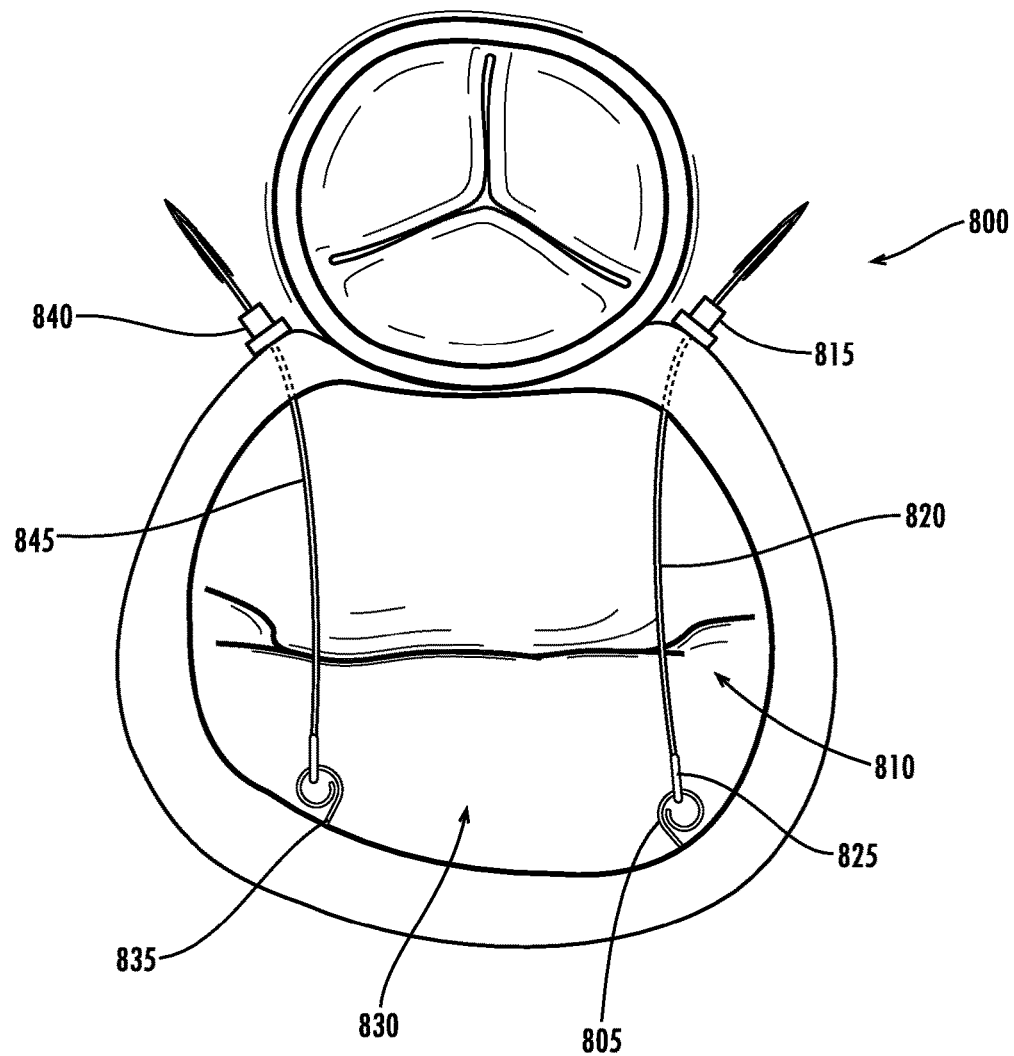
FIG. 8 provides an illustration of an exemplary embodiment of a cinching apparatus 800 in accordance with an exemplary embodiment of the present invention.

FIG. 8 provides an illustration of an exemplary embodiment of a cinching apparatus 800 in accordance with an exemplary embodiment of the present invention. The exemplary embodiment of the cinching apparatus 800, shown in FIG. 8, implements two pair of anchoring and locking components. The view shown in FIG. 8 illustrates the engagement member 805 of an anchoring component protruding into the left atrium 810. The locking component 815, can be positioned in a variety of target sites, including attachment to the wall of the left atrium 810 near the aortic valve. As shown in FIG. 8, in an exemplary embodiment, the locking component 815 can be external to the left atrium. The locking component 815 is enabled to receive the tension member 820 through a conduit in the locking component 815. Once the tension member 820 has been threaded through the locking component 815 and entered the left atrium 815, the engaging end 825 of the tension member 820 can be coupled to the engaging member 805 of an anchoring component. After coupling the tension member 820 and the anchoring component, the tension member 820 can be pulled to reduce the septal-lateral diameter of the mitral valve 830. In the exemplary embodiment shown in FIG. 8, the step of reduction can be performed outside the heart. Those of skill in the art will appreciate that the ability to perform procedures from outside the heart can be provided by many minimally invasive techniques, such as thoracoscopic, endovascular, and percutaneous deployment. Additionally, in an alternative embodiment, the steps of the methods of the present invention can be implemented via a remote device. For example, and not limitation, a surgeon could be enabled to use a remote device to adjust the tension member 820 and reduce the septal-lateral diameter of the mitral valve 830.

For example, and not limitation, the tension member 820 can extend through a long arm device outside of the patient's body. Therefore, the surgeon would have the capability to pull the tension member 820 outside of the patient's body, and thereby reduce the septal-lateral diameter of the mitral valve 830.

Those of skill in the art will appreciate that one or many sets of locking and anchoring components linked by a tension member can be implemented in an atrioventricular valve in accordance with the present invention. In some implementations, only one set of locking and anchoring components linked by a tension member is implanted. Generally, somewhere in the range of two to ten sets of locking and anchoring components linked by a tension member are implemented in an atrioventricular valve.

As shown FIG. 8, the mitral valve 830 has two sets of locking and anchoring components linked by two tension members. The second set is implemented on the opposite side of the mitral valve 830. The engaging component 835 is positioned on the opposing side of the posterior mitral annulus from engaging component 805. Similar to the other set, the locking component 840 is threaded by a tension member 845 that is then coupled to the engaging component 835. The two sets of locking and anchoring components are positioned in the exemplary embodiment shown in FIG. 8 such that the tension members, 820 and 845, run sufficiently parallel to each other. This configuration aids in maintaining the symmetry of the mitral valve 830 once its diameter is reduced. As with the first tension member 820, the tension member 845 can be extended outside the body of the patient such that the surgeon can reduce the septal-lateral diameter by the pulling the external portion of tension member 845. Once both tension member 820 and tension member 845 have been pulled to sufficiently reduce the septal-lateral diameter of the mitral valve 830, the tension members, 820 and 845, can be locked by their respective locking components, 815 and 840. The locking of the tension members 820 and 845 ensures that the desired dimensions for mitral valve 830 are maintained.

In accordance with an exemplary embodiment of the present invention, the locking component can be unlocked. In this manner, it is possible to readjust the dimension of the heart valve treated. In a non-limiting example, the valve diameter can be reduced by a certain amount and then tension member can be locked into place by the locking component. A test can then be performed to determine the competence level of the valve treated. If the competence is not to a desired level, then the tension member can be unlocked from the locking component, pulled further, and re-locked into position. Therefore, an exemplary embodiment of the present invention permits for the incremental reduction of the valve dimension over relatively extended periods of time. In one embodiment, a patient could undergo a supplemental surgery in which the locking components were accessed and the tension members further drawn to increase the reduction of the valve diameter.

The cinching apparatus of the present invention can be implemented in any of the four valves in the heart. Those of skill in the art will appreciate that each type of valve can require its own particular implementation of the cinching apparatus, wherein in the location of the components and their delivery is altered to compensate for the unique characteristics of each of the four valves.

Figure 9:
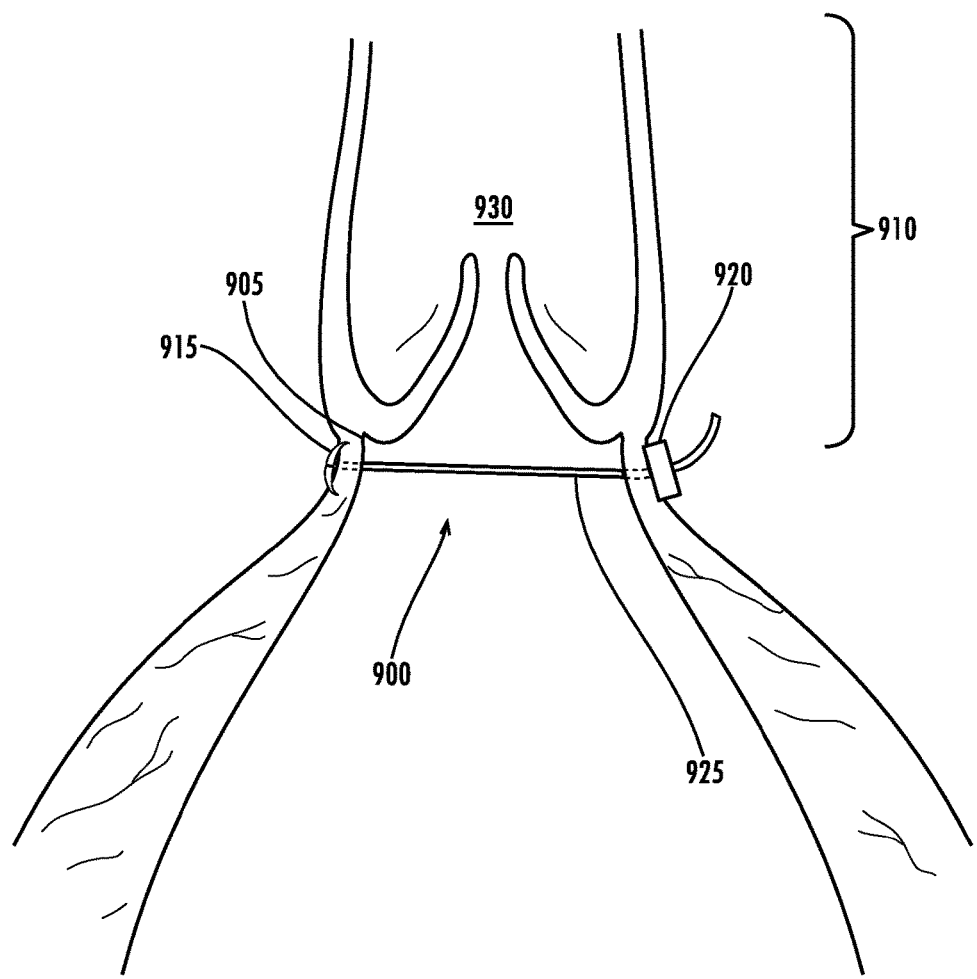
FIG. 9 provides an illustration of an exemplary embodiment of a cinching apparatus 900 implemented in an aortic valve 930 in accordance with an exemplary embodiment of the present invention.

FIG. 9 provides an illustration of an exemplary embodiment of a cinching apparatus 900 implemented in an aortic valve 930 in accordance with an exemplary embodiment of the present invention. The cinching apparatus 900 of the exemplary embodiment shown in FIG. 9 is implemented in the aortic annulus 905 of the aorta root 910. As illustrated in the exemplary embodiment shown in FIG. 9, the cinching apparatus 900 provides an anchoring component 915 that pierces the aortic annulus 905. On a substantially opposite side of the aortic annulus 905, a locking component 920 is provided that also pierces the aortic annulus 905. In an exemplary embodiment, a tension member 925 can be passed through the locking component 920 and coupled to an engaging member of the anchoring component 915. Once the tension member 925 is coupled, it can be advanced to reduce the distance between the anchoring component 915 and the locking component 920. Subsequently, the tension member 925 can be locked into place by the locking component 920. Thereby, the competence of the aortic valve 930 can be improved by enabling the cusps of the aortic valve to more completely close.

Figure 10:
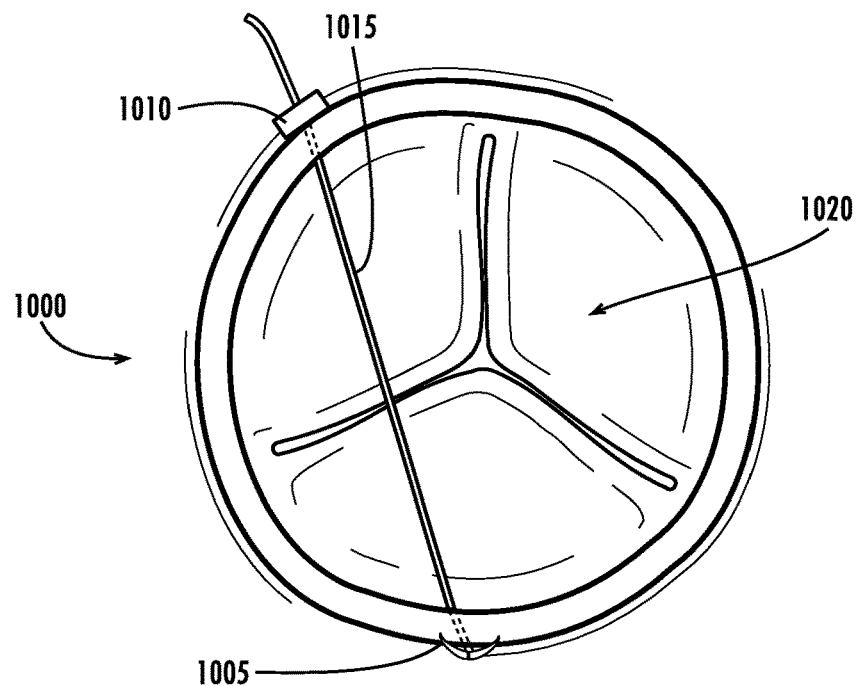
FIG. 10 provides an illustration from an apical view of an exemplary embodiment of a cinching apparatus implemented in a semilunar valve in accordance with an exemplary embodiment of the present invention.

FIG. 10 provides an illustration from an apical view of an exemplary embodiment of a cinching apparatus 1000 implemented in a semilunar valve 1020 in accordance with an exemplary embodiment of the present invention. The cinching apparatus 1000 enabled by the present invention is capable of implementation in either of the semilunar valves, the aortic or the pulmonic valve. As shown in FIG. 10, the anchoring component 1005 and the locking component 1010 can be configured on the annulus of the semilunar valve such that the tension member 1015 traverses a portion of the semilunar valve 1020. Thus, when the tension member 1015 is advanced, the diameter of the semilunar valve 1020 is decreased.

Figure 11:
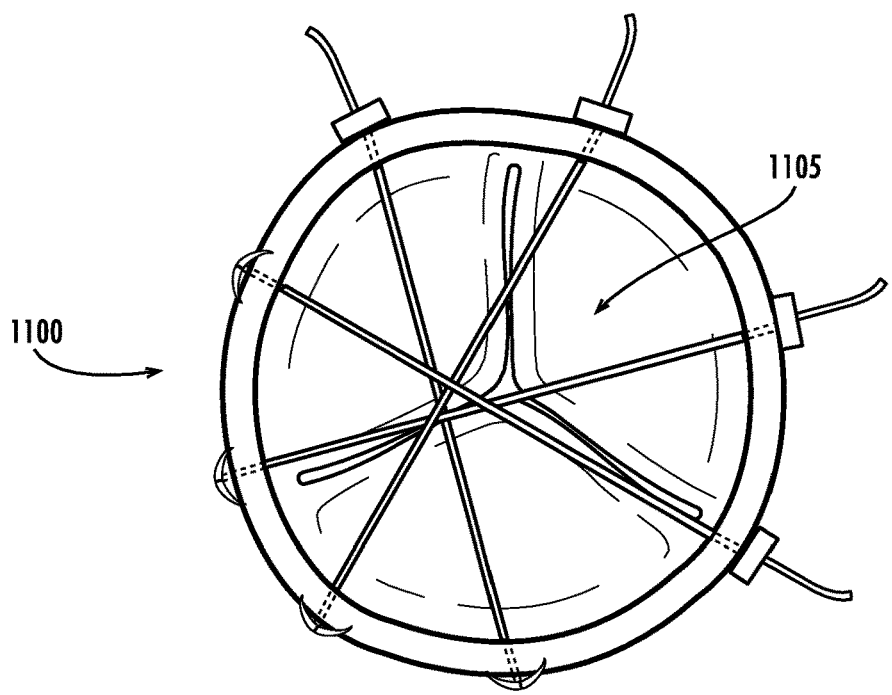
FIG. 11 provides an illustration from an apical view of an exemplary embodiment of a cinching apparatus implemented in a semilunar valve in accordance with an exemplary embodiment of the present invention.

FIG. 11 provides an illustration from an apical view of an exemplary embodiment of a cinching apparatus 1100 implemented in a semilunar valve 1105 in accordance with an exemplary embodiment of the present invention. The cinching apparatus 1100 shown in FIG. 11 includes three sets of anchoring components, locking components, and tension members. Those of skill in the art will appreciate that the number of sets of components and their implementation can vary according the particular heart valve being addressed and particular valvular condition being solved. In some implementations, the incompetence of the heart valve is less severe, thus the desired reduction in the diameter of the heart valve is relatively small. In these implementations, a limited set of components can be employed in the cinching apparatus. In other implementations, a high degree is symmetry is desired in the valve, thus the sets of components are placed to achieve and maintain a high degree of symmetry in the working valve. The exemplary embodiment shown in FIG. 11 illustrates a cinching apparatus is implemented in a semilunar valve with three sets of locking components, anchoring components, and tension members. The location of these three sets ensures a symmetrical reduction in the diameter of the semilunar valve and its improved competence and operation.

Figure 12:
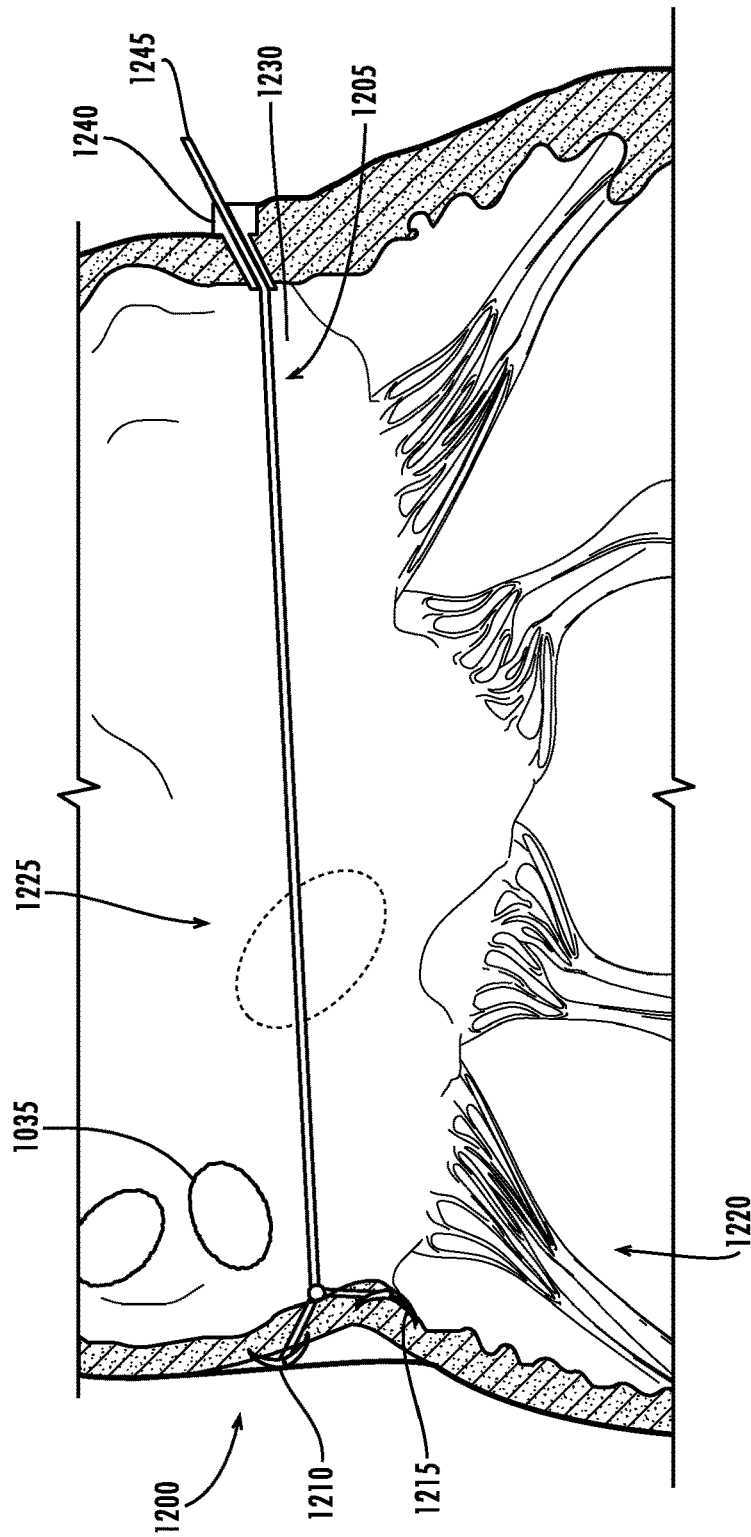
FIG. 12 provides an illustration of an exemplary embodiment of a cinching apparatus 1200 implemented in a tricuspid valve 1205 in accordance with an exemplary embodiment of the present invention.

FIG. 12 provides an illustration of an exemplary embodiment of a cinching apparatus 1200 implemented in a tricuspid valve 1205 in accordance with an exemplary embodiment of the present invention. The cinching apparatus 1200 of the exemplary embodiment shown in FIG. 12 is implemented in the annulus 1230 of the tricuspid valve 1205. As illustrated in the exemplary embodiment shown in FIG. 12, the cinching apparatus 1200 provides two anchoring components, 1210 and 1215. Similar to the embodiment of the cinching apparatus used for the mitral valve, the anchoring components, 1210 and 1215, for the tricuspid valve 1205 can be delivered in a variety of different manners. For example, and not limitation, the anchors can be percutaneously delivered via a catheter to the right ventricle 1220. Upon delivery into the right ventricle 1220, the anchoring component 1215, can be caused to pierce the tricuspid valve 1205 annulus 1230 and protrude into the right atrium 1225. Alternatively, the anchoring component 1215 could be delivered to the right atrium 1225 and then caused to pierce the tricuspid valve 1205 annulus 1230, thereby exposing the attaching member of the anchoring component 1215 in the right ventricle 1220.

In addition to the ability to mount the anchoring components between the annulus 1230 of the tricuspid valve 1205 and the right ventricle 1220, it is possible to mount the anchoring components between the annulus 1230 and the wall of the right atrium 1225. As shown in FIG. 12, anchoring component 1210 is mounted between the annulus 1230 of the tricuspid valve 1205 and the right atrium 1225. This method of attaching the anchoring component can enable additional delivery methods. For example, anchoring component 1210 can be delivered and implanted via a long arm device. A surgeon implanting an anchoring component 1210 must be careful not to implant the anchoring component 1210 in the vicinity of an opening to a coronary artery, such as opening 1235. Those of skill in the art will appreciate that an anchoring component could be delivered and implanted in a variety of different ways without detracting from the scope of the invention.

On a substantially opposite side of the annulus 1230 of the tricuspid valve 1205, a locking component 1240 can be provided. In an exemplary embodiment, the locking component 1240 can be delivered via a long arm device to the wall of the right atrium 1225. The locking component 1240 can then caused to pierce the wall of the right atrium 1225. In an exemplary embodiment, a tension member 1245 can be passed through the locking component 1240 and through the annulus 1230 of the tricuspid valve 1205. The tension member 1245 can then be coupled to the engaging members of the anchoring components, 1210 and 1215. Once the tension member 1245 is coupled, it can be advanced to reduce the distance between the anchoring components, 1210 and 1215, and the locking component 1240. Subsequently, the tension member 1245 can be locked into place by the locking component 1240. Thereby, the competence of the tricuspid valve 1205 can be improved by enabling the leaflets of the tricuspid valve 1205 to more completely close.

Figure 13:
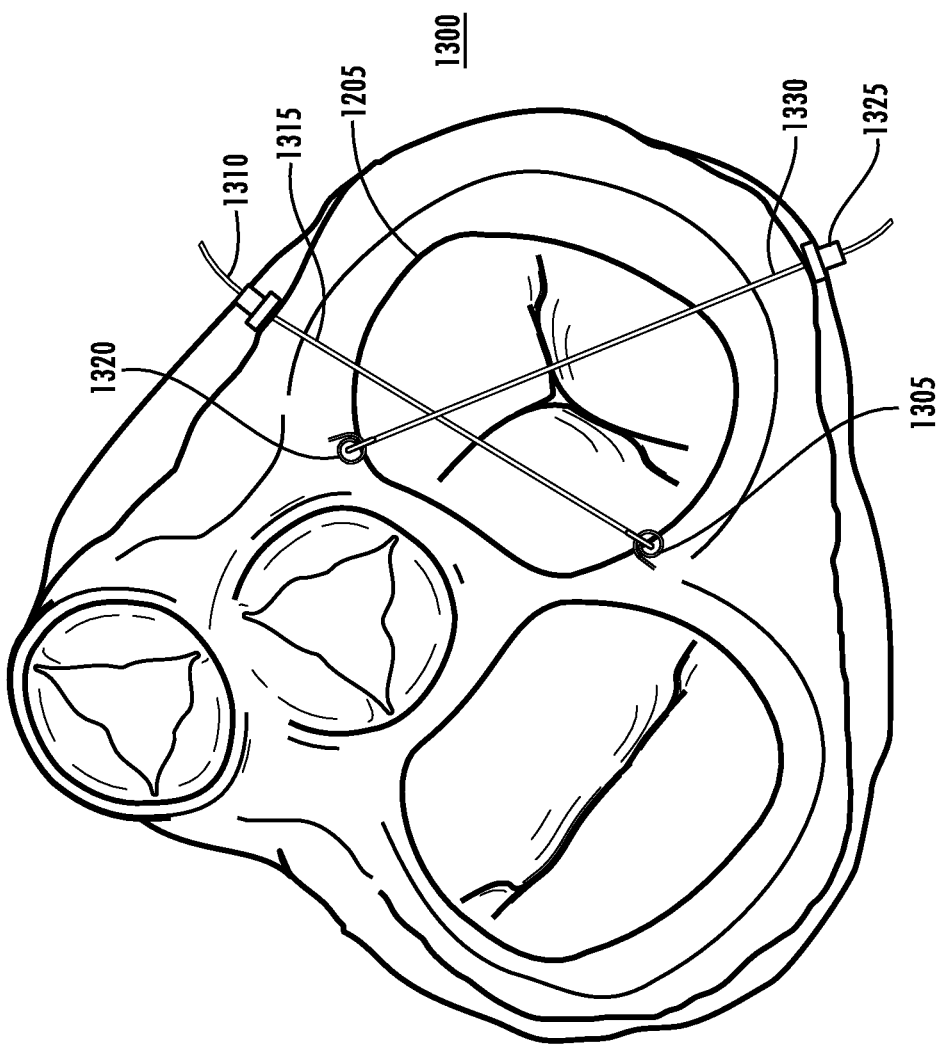
FIG. 13 provides an illustration from an apical view of an exemplary embodiment of a cinching apparatus 1300 implemented in a tricuspid valve 1205 in accordance with an exemplary embodiment of the present invention.

FIG. 13 provides an illustration from an apical view of an exemplary embodiment of a cinching apparatus 1300 implemented in a tricuspid valve 1205 in accordance with an exemplary embodiment of the present invention. As shown in FIG. 13, the cinching apparatus 1300 can include two sets of locking components, anchoring components, and tension members. A deficient tricuspid valve can most often be improved by a reduction in diameter in number of directions as the coaptation line locations for the three leaflets of the tricuspid valve 1205 are substantially irregular.

As illustrated in FIG. 13, an anchoring component 1305 can be placed on the side of the annulus of the tricuspid valve 1205 near the mitral valve. This anchoring component 1305 can then be coupled to a locking component 1310 on a substantially opposite side of the annulus by a tension member 1315. Additionally, an anchoring component 1320 can be placed on the side of the annulus near the aortic valve. Similarly, this anchoring component 1320 can be coupled to a locking component 1325 on a substantially opposite of the annulus of the tricuspid valve 1205 by a tension member 1330. When the tension members, 1315 and 1330, are advanced the diameter of the tricuspid valve 1205 is reduced. Thus, the leaflets of the tricuspid valve 1205 can more completely close and the competence of the tricuspid valve 1205 can be improved.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A cinching apparatus comprising:
    an anchoring component having a proximal end and a distal end;
    the proximal end of the anchoring component having a first attaching member enabled to piercingly attach to a tissue component of a heart;
    a tension member;
    a locking component having a second attaching member enabled to piercingly attach to a tissue component of a heart, wherein the locking component is enabled to be locked and unlocked, the locking component comprising a locking system that can be moveably positioned to lock and unlock the tension member in place at any length of a continuous portion of the tension member such that the tension member can be selectively repositioned in both a forward and a reverse direction when the locking component is unlocked;
    wherein the anchoring component is enabled to be positioned on a first target site of a tissue component of the heart and the locking component is enabled to be positioned on a second target site of a tissue component of the heart such that the locking component is positioned outside the heart, and the tension member can be coupled to both the anchoring component and the locking component; and
    wherein the tension member can be activated to adjust the distance between the first target site and the second target site and fixed by the locking component.

2. The cinching apparatus of claim 1, wherein the tension member is activated to adjust the distance between the first target site and the second target site by advancing the tension member to reduce the distance between the first target site and the second target site.

3. The cinching apparatus of claim 2, wherein the tension member is enabled to be unlocked from the locking component, further advanced, and then relocked by the locking component.

4. The cinching apparatus of claim 1, wherein the first target site is on an anterior mitral annulus and the second target site is on a posterior mitral annulus.

5. The cinching apparatus of claim 4, wherein the distance between the first target site and the second target site is the septal-lateral diameter.

6. The cinching apparatus of claim 1, wherein the first target site is on an aortic annulus and the second target site is on an aortic annulus.

7. The cinching apparatus of claim 1, wherein the first target site and the second target site are located proximate to a sino-tublar junction in an aortic root.

8. The cinching apparatus of claim 1, wherein the first target site and the second target site are located proximate to a pulmonic valve.

9. The cinching apparatus of claim 1, wherein the first target site and the second target site are located proximate to a tricuspid valve.

10. The cinching apparatus of claim 1, wherein the anchoring component is enabled to be delivered endovascularly.

11. The cinching apparatus of claim 1, wherein the locking component is enabled to be delivered with a long arm device.

12. The cinching apparatus of claim 1, wherein the tension member is enabled to be advanced from outside of a patient's body.

13. The cinching apparatus of claim 1, wherein the locking component is enabled to be activated from outside of a patient's body.

14. The cinching apparatus of claim 1, wherein the locking component is enabled to be activated on an open chest, beating heart.

15. The cinching apparatus of claim 1, wherein the tension member is a substantially smooth wire.

16. The cinching apparatus of claim 1, wherein the tension member can be selectively repositioned from outside the body via a remote device.

17. The cinching apparatus of claim 1, wherein the tension member extends through a long arm device outside of the body.

18. A septal-lateral annular cinching apparatus comprising:
an anchoring component having a proximal end and a distal end;
the proximal end of the anchoring component having a first attaching member enabled to piercingly attach to a tissue component of a heart;
the distal end of the anchoring component having a engaging member;
a tension member with an engaging distal end;
a locking component having a second attaching member enabled to piercingly attach to a tissue component of a heart, wherein the locking component is enabled to be locked and unlocked, the locking component comprising a locking system that can be moveably positioned to lock and unlock the tension member in place such that the tension member can be selectively repositioned in both a forward and a reverse direction when the locking component is unlocked, wherein the tension member is substantially smooth;
wherein the anchoring component is enabled to be positioned on a first target site of a tissue component of the heart and the locking component is enabled to be positioned on a second target site of a tissue component of the heart such that the locking component is positioned outside the heart, the tension member can be passed through the locking component, and the engaging distal end of the tension member can be coupled to the distal end of the anchoring component; and
wherein the tension member can be advanced to reduce the distance between the first target site and the second target site and fixed by the locking component.

19. The septal-lateral annular cinching apparatus of claim 18, wherein the tension member can be unlocked from the locking component, advanced, and then relocked by the locking component.

20. The septal-lateral annular cinching apparatus of claim 18, wherein the first and second target sites are located proximate a mitral valve annulus.

* * * * *

UNITED STATES PATENT AND TRADEMARK OFFICE
CERTIFICATE OF CORRECTION

| | | |
|---|---|---|
| PATENT NO. | : 10,039,531 B2 | Page 1 of 1 |
| APPLICATION NO. | : 12/097318 | |
| DATED | : August 7, 2018 | |
| INVENTOR(S) | : Yoganathan et al. | |

It is certified that error appears in the above-identified patent and that said Letters Patent is hereby corrected as shown below:

In the Specification

At Column 1, Line 4, please insert the following paragraph:
-- STATEMENT REGARDING FEDERALLY SPONSORED RESEARCH
This invention was made with U.S. government support under Contract No. R01 HL052009 awarded by National Institutes of Health. The government has certain rights in the invention. --

Signed and Sealed this
Sixth Day of November, 2018

Andrei Iancu
*Director of the United States Patent and Trademark Office*